United States Patent [19]
Streit

[11] Patent Number: 6,143,955
[45] Date of Patent: Nov. 7, 2000

[54] SOYBEAN VARIETY 93B07

[75] Inventor: Leon George Streit, Johnston, Iowa

[73] Assignee: Pioneer Hi-Bred International, Inc., Des Moines, Iowa

[21] Appl. No.: 09/240,488

[22] Filed: Jan. 29, 1999

[51] Int. Cl.$^7$ .............................. A01H 1/04; A01H 5/00; A01H 5/10; C12N 5/04

[52] U.S. Cl. .................... 800/312; 800/260; 800/266; 800/267; 800/268; 800/278; 435/415; 435/421; 435/426; 435/430; 435/430.1; 435/468

[58] Field of Search ................................. 800/260, 266, 800/267, 268, 278, 312; 435/415, 421, 426, 430, 430.1, 468

[56] References Cited

U.S. PATENT DOCUMENTS

| | | | |
|---|---|---|---|
| 4,545,146 | 10/1985 | Davis | 47/58 |
| 5,534,425 | 7/1996 | Fehr et al. | 435/172.1 |
| 5,824,844 | 10/1998 | Streit et al. | 800/200 |

OTHER PUBLICATIONS

Jaycox, "Ecological Relationships between Honey Bees and Soybeans," *American Bee Journal* vol. 110(8):306–307 (Aug. 1970).

Komatsuda, T. et al., Maturation and Germination of Somatic Embryos as Affected by Sucrose and Plant Growth Regulators in Soybeans Glycine gracilis Skvortz and Glycine max (L.) Merr., *Plant Cell, Tissue and Organ Culture*, 28:103–113, 1992.

Dhir, S. et al., "Regeneration of Fertile Plants from Protoplasts of Soybean (Glycine max L. Merr.): Genotypic Differences in Culture Response," *Plant Cell Reports* (1992) 11:285–289.

Pandey, P. et al., "Plant Regeneration from Leaf and Hypocotyl Explants of Glycine wightii (W. and A.) Verdc. var longicauda," *Japan J. Breed*. 42:1–5 (1992).

Shetty, K. et al., "Stimulation of In Vitro Shoot Organogenesis in Glycine max (Merrill.) by Allantoin and Amides," Plant Science 81:(1992) 245–251.

Stephens, P.A. et al., "Agronomic Evaluation of Tissue–Culture–Derived Soybean Plants," *Theor. Appl. Genet.* (1991) 82:633–635.

Komatsuda, T. et al., "Genotype X Sucrose Interactions for Somatic Embryogenesis in Soybean," *Crop Sci.* 31:333–337 (1991).

"Economic Implications of Modified Soybean Traits Summary Report", Iowa Soybean Promotion Board & American Soybean Association Special Report 92S, May 1990.

Caldwell, B. E. 2nd ed. 1989, "Soybeans: Improvement, Production, and Uses" Amer. Soc. Agron. Monograph No. 16, Chapter 17.

Buttery, B. R., and R. I. Buzzell 1968. "Peroxidase Activity in Seed of Soybean Varieties" Crop Sci. 8: 722–725.

Hymowitz, T. 1973. "Electrophoretic analysis of SBTI–A2 in the USDA Soybean Germplasm Collection" Crop Sci., 13: 420–421.

Payne R. C., and L.F. Morris, 1976. "Differentiation of Soybean Cultivars by Seedling Pigmentation Patterns" J. Seed. Technol. 1: 1–19.

*Primary Examiner*—David T. Fox
*Attorney, Agent, or Firm*—Pioneer Hi-Bred International, Inc.

[57] ABSTRACT

A soybean variety designated 93B07, the plants and seeds of soybean variety 93B07, methods for producing a soybean plant produced by crossing the variety 93B07 with itself or with another soybean plant, and hybrid soybean seeds and plants produced by crossing the variety 93B07 with another soybean line or plant, and the creation of variants by mutagenesis or transformation of variety 93B07. This invention also relates to methods for producing other soybean varieties or breeding lines derived from soybean variety 93B07 and to soybean varieties or breeding lines produced by those methods.

27 Claims, No Drawings

SOYBEAN VARIETY 93B07

FIELD OF THE INVENTION

This invention is in the field of soybean breeding, specifically relating to a soybean variety designated 93B07.

BACKGROUND OF THE INVENTION

The present invention relates to a new and distinctive soybean variety, designated 93B07 which has been the result of years of careful breeding and selection as part of a soybean program. There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety an improved combination of desirable traits from the parental germplasm. These important traits may include higher seed yield, resistance to diseases and insects, tolerance to drought and heat, and better agronomic qualities.

Field crops are bred through techniques that take advantage of the plant's method of pollination. A plant is self-pollinated if pollen from one flower is transferred to the same or another flower of the same plant. A plant is cross-pollinated if the pollen comes from a flower on a different plant. Soybean plants (*Glycine max*), are recognized to be naturally self-pollinated plants which, while capable of undergoing cross-pollination, rarely do so in nature. Insects are reported by some researchers to carry pollen from one soybean plant to another and it generally is estimated that less than one percent of soybean seed formed in an open planting can be traced to cross-pollination, i.e. less than one percent of soybean seed formed in an open planting is capable of producing $F_1$ hybrid soybean plants, See Jaycox, "Ecological Relationships between Honey Bees and Soybeans," appearing in the American Bee Journal Vol. 110(8): 306–307 (August 1970). Thus intervention for control of pollination is critical to establishment of superior varieties.

A cross between two different homozygous lines produces a uniform population of hybrid plants that may be heterozygous for many gene loci. A cross of two plants each heterozygous at a number of gene loci will produce a population of hybrid plants that differ genetically and will not be uniform. Regardless of parentage, plants that have been self-pollinated and selected for type for many generations become homozygous at almost all gene loci and produce a uniform population of true breeding progeny.

Soybeans, (*Glycine max*), can be bred by both self-pollination and cross-pollination techniques. Choice of breeding or selection methods depends on the mode of plant reproduction, the heritability of the trait(s) being improved, and the type of variety used commercially (e.g., $F_1$ hybrid variety, pureline variety, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Pedigree breeding and recurrent selection breeding methods are used to develop varieties from breeding populations. Pedigree breeding starts with the crossing of two genotypes, each of which may have one or more desirable characteristics that is lacking in the other or which complements the other. If the two original parents do not provide all the desired characteristics, other sources can be included in the breeding population. In the pedigree method, superior plants are selfed and selected in successive generations. In the succeeding generations the heterozygous condition gives way to homogeneous lines as a result of self-pollination and selection. Typically in the pedigree method of breeding five or more generations of selfing and selection is practiced: $F_1 \rightarrow F_2$; $F_2 \rightarrow F_3$; $F_3 \rightarrow F_4$; $F_4 \rightarrow F_5$, etc.

Pedigree breeding is commonly used for the improvement of self-pollinating crops. Two parents that possess favorable, complementary traits are crossed to produce an $F_1$. An $F_2$ population is produced by selfing one or several $F_1$'s or by intercrossing two $F_1$'s (sib mating). Selection of the best individuals may begin in the $F_2$ population; then, beginning in the $F_3$, the best individuals in the best families are selected. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new varieties.

Backcross breeding has been used to transfer genes for simply inherited, highly heritable traits into a desirable homozygous variety or inbred line that is utilized as the recurrent parent. The source of the traits to be transferred is called the donor parent. After the initial cross, individuals possessing the desired traits of the donor parent are selected and repeatedly crossed (backcrossed) to the recurrent parent. The resulting plant is expected to have the attributes of the recurrent parent (e.g., variety) and the desirable traits transferred from the donor parent. This approach has been used extensively for breeding disease resistant varieties.

Each soybean breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful varieties produced per unit of input (e.g., per year, per dollar expended, etc.).

Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Promising advanced breeding lines are thoroughly tested and compared to appropriate standards in environments representative of the commercial target area(s) for three or more years. The best lines are candidates for new commercial varieties; those still deficient in a few traits may be used as parents to produce new populations for further selection.

Publically available or newly-released varieties of soybean can also be used as parental lines or starting materials for breeding or as source populations from which to develop or derive other soybean varieties or breeding lines. These varieties or lines derived from publicly available or newly-released varieties can be developed by using breeding methods described earlier, such as pedigree breeding, backcrossing and recurrent selection. As an example, when backcross breeding is used to create these derived lines or varieties in a soybean breeding program, publicly available or newly released varieties of soybeans can be used as a parental line or starting material or source population and can serve as either the donor or recurrent parent. See for example, Fehr, "Breeding Methods for Cultivar Development", Chapter 7, *Soybeans Improvement, Production and Uses*, $2^{nd}$ ed., Wilcox ed. 1987.

These processes, which lead to the final step of marketing and distribution, can take from eight to twelve years from the time the first cross is made. Therefore, development of new varieties is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard variety. Generally a single observation is inconclusive, so replicated observations are required to provide a better estimate of its genetic worth.

In addition to the preceding problem, it is not known how the genotype will react with the environment. This genotype by environment interaction is an important, yet unpredictable, factor in plant breeding. A breeder of ordinary skill in the art cannot predict the genotype, how that genotype will interact with various environments or the resulting phenotypes of the developing lines, except perhaps in a very broad and general fashion. A breeder of ordinary skill in the art would also be unable to recreate the same line twice from the very same original parents, as the breeder is unable to direct how the genomes combine or how they will interact with the environmental conditions. This unpredictability results in the expenditure of large amounts of research resources in the development of a superior new soybean variety.

The goal of soybean breeding is to develop new, unique and superior soybean varieties. In practical application of a chosen soybean breeding program, the breeder initially selects and crosses two or more parental lines, followed by repeated selfing and selection, producing many new genetic combinations. The breeder can theoretically generate billions of different genetic combinations via crossing, selfing and mutations. The breeder has no direct control at the cellular level. Therefore, two breeders will never develop the same line, or even very similar lines, having the same soybean traits.

Each year, the plant breeder selects the germplasm to advance to the next generation. This germplasm is grown under unique and different geographical, climatic and soil conditions, and further selections are then made during and at the end of the growing season. The varieties which are developed are unpredictable for the reasons already mentioned.

Mass and recurrent selections can be used to improve populations of either self- or cross-pollinated crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In a multiple-seed procedure, soybean breeders commonly harvest one or more pods from each plant in a population and thresh them together to form a bulk. Part of the bulk is used to plant the next generation and part is put in reserve. The procedure has been referred to as modified single-seed descent or the pod-bulk technique.

The multiple-seed procedure has been used to save labor at harvest. It is considerably faster to thresh pods with a machine than to remove one seed from each by hand for the single-seed procedure. The multiple-seed procedure also makes it possible to plant the same number of seeds of a population each generation of inbreeding. Enough seeds are harvested to make up for those plants that did not germinate or produce seed.

Descriptions of other breeding methods that are commonly used for different traits and crops can be found in one of several reference books (e.g., Allard, 1960; Simmonds, 1979; Sneep et al., 1979; Fehr, 1987).

Proper testing should detect major faults and establish the level of superiority or improvement over current varieties. In addition to showing superior performance, there must be a demand for a new variety. The new variety must be compatible with industry standards, or must create a new market. The introduction of a new variety may incur additional costs to the seed producer, the grower, processor and consumer, for special advertising and marketing, altered seed and commercial production practices, and new product utilization. The testing preceding release of a new variety should take into consideration research and development costs as well as technical superiority of the final variety. For seed-propagated varieties, it must be feasible to produce seed easily and economically.

Soybean (*Glycine max*), is an important and valuable field crop. Thus, a continuing goal of soybean breeders is to develop stable, high yielding soybean varieties that are agronomically sound. The reasons for this goal are obviously to maximize the amount of grain produced on the land used and to supply food for both animals and humans. To accomplish this goal, the soybean breeder must select and develop soybean plants that have the traits that result in superior varieties.

Pioneer soybean research staff create over 500,000 potential new varieties each year. Of those new varieties, less than 50 and more commonly less than 25 are actually selected for commercial use.

SUMMARY OF THE INVENTION

According to the invention, there is provided a novel soybean variety, designated 93B07. This invention thus relates to the seeds of soybean variety 93B07, to the plants of soybean 93B07 and to methods for producing a soybean plant produced by crossing soybean variety 93B07 with itself or another soybean plant, and the creation of variants by mutagenesis or transformation of soybean 93B07. This invention also relates to methods for producing other soybean varieties or breeding lines derived from soybean variety 93B07 and to soybean varieties or breeding lines produced by those methods.

DEFINITIONS

In the description and tables which follow, a number of terms are used. In order to provide a clear and consistent understanding of the specification and claims, including the scope to be given such terms, the following definitions are provided:

B/A=BUSHELS PER ACRE. The seed yield in bushels/acre is the actual yield of the grain at harvest.

BSR=BROWN STEM ROT TOLERANCE. This is a visual disease score from 1 to 9 comparing all genotypes in a given test. The score is based on leaf symptoms of yellowing and necrosis caused by brown stem rot. A score of 9 indicates no symptoms. Visual scores range down to a score of 1 which indicates severe symptoms of leaf yellowing and necrosis.

CNKR=STEM CANKER TOLERANCE. This is a visual disease score from 1 to 9 comparing all genotypes in a given test. The score is based upon premature plant death. A score of 9 indicates no symptoms, whereas a score of 1 indicates the entire experimental unit died very early.

COTYLEDON. A cotyledon is a type of seed leaf. The cotyledon contains the food storage tissues of the seed.

EMBRYO. The embryo is the small plant contained within a mature seed.

$F_3$. This symbol denotes a generation resulting from the selfing of the $F_2$ generation along with selection for type and rogueing of off-types. The "F" number is a term commonly used in genetics, and designates the number of the filial generation. The "$F_3$" generation denotes the offspring resulting from the selfing or self mating of members of the generation having the next lower "F" number, viz. the $F_2$ generation.

FECL=IRON-DEFICIENCY CHLOROSIS. Plants are scored 1 to 9 based on visual observations. A score of 1 indicates the plants are dead or dying from iron-deficiency chlorosis, a score of 5 means plants have intermediate health with some leaf yellowing and a score of 9 means no stunting of the plants or yellowing of the leaves.

FEY=Frogeye Tolerance. This is a visual disease score from 1 to 9 comparing all genotypes in a given test. The score is based upon leaf lesions. A score of 9 indicates no lesions, whereas a score of 1 indicates severe leaf necrosis.

HABIT. This refers to the physical appearance of a plant. It can be either determinate or indeterminate. In soybeans, indeterminate varieties are those in which stem growth is not limited by formation of a reproductive structure (i.e., flowers, pods and seeds) and hence growth continues throughout flowering and during part of pod filling. The main stem will develop and set pods over a prolonged period under favorable conditions. In soybeans, determinate varieties are those in which stem growth ceases at flowering time. Most flowers develop simultaneously, and most pods fill at approximately the same time.

HGT=Plant Height. Plant height is taken from the top of the soil to top pod of the plant and is measured in inches.

HILUM. This refers to the scar left on the seed which marks the place where the seed was attached to the pod prior to it (the seed) being harvested.

HYPL=HYPOCOTYL ELONGATION. This score indicates the ability of the seed to emerge when planted 3" deep in sand and with a controlled temperature of 25° C. The number of plants that emerge each day are counted. Based on this data, each genotype is given a 1 to 9 score based on its rate of emergence and percent of emergence. A score of 9 indicates an excellent rate and percent of emergence, an intermediate score of 5 indicates average ratings and a 1 score indicates a very poor rate and percent of emergence.

HYPOCOTYL. A hypocotyl is the portion of an embryo or seedling between the cotyledons and the root. Therefore, it can be considered a transition zone between shoot and root.

LDG=LODGING RESISTANCE. Lodging is rated on a scale of 1 to 9. A score of 9 indicates erect plants. A score of 5 indicates plants are leaning at a 45° angle in relation to the ground and a score of 1 indicates plants are laying on the ground.

LEAFLETS. These are part of the plant shoot, and they manufacture food for the plant by the process of photosynthesis.

LLE=Linoleic Acid Percent. Linoleic acid is one of the five most abundant fatty acids in soybean seeds. It is measured by gas chromatography and is reported as a percent of the total oil content.

LLN=Linolenic Acid Percent. Linolenic acid is one of the five most abundant fatty acids in soybean seeds. It is measured by gas chromatography and is reported as a percent of the total oil content.

MAT ABS=ABSOLUTE MATURITY. This term is defined as the length of time from planting to complete physiological development (maturity). The period from planting until maturity is reached is measured in days, usually in comparison to one or more standard varieties. Plants are considered mature when 95% of the pods have reached their mature color.

MATURITY GROUP. This refers to an agreed-on industry division of groups of varieties, based on the zones in which they are adapted primarily according to day length or latitude. They consist of very long day length varieties (Groups 000, 00, 0), and extend to very short day length varieties (Groups VII, VIII, IX, X).

OIL=Oil Percent. Soybean seeds contain a considerable amount of oil. Oil is measured by NIR spectrophotometry, and is reported on an as is percentage basis.

OLC=OLEIC ACID PERCENT. Oleic acid is one of the five most abundant fatty acids in soybean seeds. It is measured by gas chromatography and is reported as a percent of the total oil content.

PLM=Palmitic Acid Percent. Palmitic acid is one of the five most abundant fatty acids in soybean seeds. It is measured by gas chromatography and is reported as a percent of the total oil content.

POD. This refers to the fruit of a soybean plant. It consists of the hull or shell (pericarp) and the soybean seeds.

PRT=PHYTOPHTHORA TOLERANCE. Tolerance to Phytophthora root rot is rated on a scale of 1 to 9, with a score of 9 being the best or highest tolerance ranging down to a score of 1 which indicates the plants have no tolerance to Phytophthora.

PRM=Predicted Relative Maturity. Soybean maturities are divided into relative maturity groups. In the United States the most common maturity groups are 0 through VIII. Within these maturity groups the industry generally divides maturities into tenths of a relative maturity group. Within narrow comparisons, the difference of a tenth of a relative maturity group equates very roughly to a day difference in maturity at harvest.

PRO=Protein Percent. Soybean seeds contain a considerable amount of protein. Protein is generally measured by NIR spectrophotometry and is reported on an as is percentage basis.

PUBESCENCE. This refers to a covering of very fine hairs closely arranged on the leaves, stems and pods of the soybean plant.

SDS=Sudden Death Syndrome. Tolerance to Sudden Death Syndrome is rated on a scale of 1 to 9, with a score of 1 being very susceptible ranging up to a score of 9 being resistant.

S/LB=Seeds per Pound. Soybean seeds vary in seed size, therefore, the number of seeds required to make up one pound also varies. This affects the pounds of seed required to plant a given area, and can also impact end uses.

SH=SHATTERING. This refers to the amount of pod dehiscence prior to harvest. Pod dehiscence involves seeds falling from the pods to the soil. This is a visual score from 1 to 9 comparing all genotypes within a given test. A score of 9 means pods have not opened and no seeds have fallen out. A score of 5 indicates approximately 50% of the pods have opened, with seeds falling to the ground and a score of 1 indicates 100% of the pods are opened.

SHOOTS. These are a portion of the body of the plant. They consist of stems, petioles and leaves.

STC=STEARIC ACID PERCENT. Stearic acid is one of the five most abundant fatty acids in soybean seeds. It is measured by gas chromatography and is reported as a percent of the total oil content.

WH MD=WHITE MOLD TOLERANCE. This is a visual disease score from 1 to 9 comparing all genotypes in a given test. The score is based upon observations of mycelial growth and death of plants. A score of 9 indicates no symptoms. Visual scores of 1 indicate complete death of the experimental unit.

DETAILED DESCRIPTION OF THE INVENTION

A soybean variety needs to be highly homogeneous, homozygous and reproducible to be useful as a commercial variety. There are many analytical methods available to determine the homozygotic and phenotypic stability of these inbred lines.

The oldest and most traditional method of analysis is the observation of phenotypic traits. The data is usually collected in field experiments over the life of the soybean plants to be examined. Phenotypic characteristics most often observed are for traits associated with seed yield, seed protein and oil content, lodging resistance, disease resistance, maturity, plant height, and shattering.

In addition to phenotypic observations, the genotype of a plant can also be examined. There are many laboratory-based techniques available for the analysis, comparison and characterization of plant genotype; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), and Simple Sequence Repeats (SSRs) which are also referred to as Microsatellites.

The variety of the invention has shown uniformity and stability for all traits, as described in the following variety description information. It has been self-pollinated a sufficient number of generations, with careful attention to uniformity of plant type to ensure homozygosity and phenotypic stability. The line has been increased with continued observation for uniformity. No variant traits have been observed or are expected in 93B07, as described in Table 1 (Variety Description Information).

Soybean variety 93B07 is a white flowered, soybean variety with gray pubescence and buff hila. 93B07 demonstrates excellent field emergence and multi-race Phytophthora resistance (Rps1c). Variety 93B07 further demonstrates above average resistance to lodging as well as resistance to races 3 and 14 of soybean Cyst Nematode. This variety further displays a substantial degree of glyphosate resistance. Variety 93B07 is particularly suited to the Plains, Eastern, and Northern regions of the United States including Southern Iowa, Northern Illinois, and Indiana. This variety does well in a variety of soils including those which are light and sandy, no-till, infected with Soybean cyst Nematode and/or infected with *Phytophthora megasperma*.

Soybean variety 93B07, being substantially homozygous, can be reproduced by planting seeds of the line, growing the resulting soybean plants under self-pollinating or sib-pollinating conditions, and harvesting the resulting seed, using techniques familiar to the agricultural arts.

TABLE 1

VARIETY DESCRIPTION INFORMATION
93B07

A. Mature Seed Characteristics:

Seed Coat Color: yellow
Seed Coat Luster: dull
Seed Size (grams per 100 seeds): 16
Hilum Color: buff
Cotyledon Color: yellow
Seed Protein Peroxidase: high B. Leaf:

Leaflet Shape: ovate
Leaf Color: medium green

C. Plant Characteristics:

Flower Color: white
Pod Color: brown
Plant Pubescence Color: gray
Plant Types: intermediate
Plant Habit: indeterminate
Maturity Group: III D. Fungal Diseases (S = susceptible R = resistant)

Brown Stem Rot (*Cephalosporium gregatum*): moderately susceptible
Phytophthora Rot (*Phytophthora megasperma* var. *sojae*):
    Race 1: R    Race 3: R    Race 4: S
    Race 7: R
SDS: susceptible
Sclerotinia: susceptible E. Nematode Diseases (S = susceptible R = resistant)

Soybean Cyst Nematode
    Race 3: resistant
Soybean Cyst Other: resistant
Soybean Cyst Other Specify: 14
Iron Chlorosis: moderately susceptible F. Submitted Seed Content (% Protein): 36
Submitted Seed Content (% Oil): 19

Publications useful as references in interpreting Table 1 include:
Caldwell, B. E. ed. 1973. "Soybeans: Improvement, Production, and Uses" Amer. Soc. Agron. Monograph No. 16;
Buttery, B. R., and R. I. Buzzell 1968. "Peroxidase Activity in Seed of Soybean Varieties" Crop Sci. 8: 722–725;
Hymowitz, T. 1973. "Electrophoretic analysis of SBTI-A2 in the USDA Soybean Germplasm Collection" Crop Sci., 13: 420–421;
Payne R. C., and L. F. Morris, 1976. "Differentiation of Soybean Varieties by Seedling Pigmentation Patterns" J. Seed. Technol. 1: 1–19. The disclosures of which are each incorporated by reference in their entirety.

FURTHER EMBODIMENTS OF THE INVENTION

Transformation of Soybean

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Such foreign, additional and/or modified genes are referred to herein collectively as "transgenes". Over the last fifteen to twenty years several methods for producing transgenic plants have been developed, and the present invention, in particular embodiments, also relates to transformed versions of the claimed variety or line.

Plant transformation involves the construction of an expression vector which will function in plant cells. Such a vector comprises DNA comprising a gene under control of or operatively linked to a regulatory element (for example, a promoter). The expression vector may contain one or more such operably linked gene/regulatory element combinations. The vector(s) may be in the form of a plasmid, and can be used alone or in combination with other plasmids, to provide transformed soybean plants, using transformation methods as described below to incorporate transgenes into the genetic material of the soybean plant(s).

Expression Vectors for Soybean Transformation
Marker Genes

Expression vectors include at least one genetic marker, operably linked to a regulatory element (a promoter, for example) that allows transformed cells containing the marker to be either recovered by negative selection, i.e. inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or a herbicide, or genes that encode an altered target which is insensitive to the inhibitor. A few positive selection methods are also known in the art.

One commonly used selectable marker gene for plant transformation is the neomycin phosphotransferase II (nptII) gene, isolated from transposon Tn5, which when placed under the control of plant regulatory signals confers resistance to kanamycin. Fraley et al., *Proc. Natl. Acad. Sci. U.S.A.*, 80: 4803 (1983). Another commonly used selectable marker gene is the hygromycin phosphotransferase gene which confers resistance to the antibiotic hygromycin. Vanden Elzen et al., *Plant Mol. Biol.*, 5: 299 (1985).

Additional selectable marker genes of bacterial origin that confer resistance to antibiotics include gentamycin acetyl transferase, streptomycin phosphotransferase, aminoglycoside-3'-adenyl transferase, the bleomycin resistance determinant. Hayford et al., *Plant Physiol.* 86: 1216 (1988), Jones et al., *Mol. Gen. Genet.*, 210: 86 (1987), Svab et al., *Plant Mol. Biol.* 14: 197 (1990), Hille et al., *Plant Mol. Biol.* 7: 171 (1986). Other selectable marker genes confer resistance to herbicides such as glyphosate, glufosinate or broxynil. Comai et al., *Nature* 317: 741–744 (1985), Gordon-Kamm et al., *Plant Cell* 2: 603–618 (1990) and Stalker et al., *Science* 242: 419–423 (1988).

Other selectable marker genes for plant transformation are not of bacterial origin. These genes include, for example, mouse dihydrofolate reductase, plant 5-enolpyruvylshikimate-3-phosphate synthase and plant acetolactate synthase. Eichholtz et al., *Somatic Cell Mol. Genet.* 13: 67 (1987), Shah et al., *Science* 233: 478 (1986), Charest et al., *Plant Cell Rep.* 8: 643 (1990).

Another class of marker genes for plant transformation require screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include β-glucuronidase (GUS), β-galactosidase, luciferase and chloramphenicol acetyltransferase. Jefferson, R. A., *Plant Mol. Biol. Rep.* 5: 387 (1987)., Teeri et al., *EMBO J.* 8: 343 (1989), Koncz et al., *Proc. Natl. Acad. Sci. U.S.A.* 84:131 (1987), De Block et al., *EMBO J.* 3: 1681 (1984).

Recently, in vivo methods for visualizing GUS activity that do not require destruction of plant tissue have been made available. Molecular Probes Publication 2908, Imagene Green™, p. 1–4 (1993) and Naleway et al., *J. Cell Biol.* 115: 15Ia (1991). However, these in vivo methods for visualizing GUS activity have not proven useful for recovery of transformed cells because of low sensitivity, high fluorescent backgrounds and limitations associated with the use of luciferase genes as selectable markers.

More recently, a gene encoding Green Fluorescent Protein (GFP) has been utilized as a marker for gene expression in prokaryotic and eukaryotic cells. Chalfie et al., *Science* 263: 802 (1994). GFP and mutants of GFP may be used as screenable markers.

Promoters

Genes included in expression vectors must be driven by a nucleotide sequence comprising a regulatory element, for example, a promoter. Several types of promoters are now well known in the transformation arts, as are other regulatory elements that can be used alone or in combination with promoters.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters which initiate transcription only in certain tissue are referred to as "tissue-specific". A "cell type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter is a promoter which is active under most environmental conditions.

A. Inducible Promoters

An inducible promoter is operably linked to a gene for expression in soybean. Optionally, the inducible promoter is operably linked to a nucleotide sequence encoding a signal sequence which is operably linked to a gene for expression in soybean. With an inducible promoter the rate of transcription increases in response to an inducing agent.

Any inducible promoter can be used in the instant invention. See Ward et al. *Plant Mol. Biol.*22: 361–366 (1993). Exemplary inducible promoters include, but are not limited to, that from the ACEI system which responds to copper (Mett et al. *PNAS* 90: 4567–4571 (1993)); In2 gene from maize which responds to benzenesulfonamide herbicide safeners (Hershey et al., *Mol. Gen. Genetics* 227: 229–237 (1991) and Gatz et al., *Mol. Gen. Genetics* 243: 32–38 (1994)) or Tet repressor from Tn10 (Gatz et al., *Mol. Gen. Genet.* 227: 229–237 (1991). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone. Schena et al., *Proc. Natl. Acad. Sci. U.S.A.* 88: 0421 (1991).

B. Constitutive Promoters

A constitutive promoter is operably linked to a gene for expression in soybean or the constitutive promoter is operably linked to a nucleotide sequence encoding a signal sequence which is operably linked to a gene for expression in soybean.

Many different constitutive promoters can be utilized in the instant invention. Exemplary constitutive promoters include, but are not limited to, the promoters from plant viruses such as the 35S promoter from CaMV (Odell et al., *Nature* 313: 810–812 (1985) and the promoters from such genes as rice actin (McElroy et al., *Plant Cell* 2: 163–171 (1990)); ubiquitin (Christensen et al., *Plant Mol. Biol.*12: 619–632 (1989) and Christensen et al., *Plant Mol. Biol.* 18: 675–689 (1992)); pEMU (Last et al., *Theor. Appl. Genet.* 81: 581–588 (1991)); MAS (Velten et al., *EMBO J.* 3: 2723–2730 (1984)) and maize H3 histone (Lepetit et al., *Mol. Gen. Genet.*231: 276–285 (1992) and Atanassova et al., *Plant Journal* 2 (3): 291–300 (1992)).

The ALS promoter, a XbaI/NcoI fragment 5' to the *Brassica napus* ALS3 structural gene (or a nucleotide sequence that has substantial sequence similarity to said XbaI/NcoI fragment), represents a particularly useful constitutive promoter. See PCT application WO96/30530.

C. Tissue-specific or Tissue-preferred Promoters

A tissue-specific promoter is operably linked to a gene for expression in soybean. Optionally, the tissue-specific promoter is operably linked to a nucleotide sequence encoding a signal sequence which is operably linked to a gene for expression in soybean. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter- such as that from the phaseolin gene (Murai et al., *Science* 23: 476–482 (1983) and Sengupta-Gopalan et al., *Proc. Natl. Acad. Sci. USA* 82: 3320–3324 (1985)); a leaf-specific and light-induced promoter such as that from cab or rubisco (Simpson et al., *EMBO J.* 4(11): 2723–2729 (1985) and Timko et al., *Nature* 318: 579–582 (1985)); an anther-specific promoter such as that from LAT52 (Twell et al., *Mol. Gen. Genet.* 217: 240–245 (1989)); a pollen-specific promoter such as that from Zm13 (Guerrero et al., *Mol. Gen. Genet.*224: 161–168 (1993)) or a microspore-preferred promoter such as that from apg (Twell et al., *Sex. Plant Reprod.* 6: 217–224 (1993).

Signal Sequences for Targeting Proteins to Subcellular Compartments

Transport of protein produced by transgenes to a subcellular compartment such as the chloroplast, vacuole, peroxisome, glyoxysome, cell wall or mitochondrion, or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example, Becker et al., *Plant Mol. Biol.*20: 49 (1992), Close, P. S., Master's Thesis, Iowa State University (1993), Knox, C., et al., "Structure and Organization of Two Divergent Alpha-Amylase Genes From Barley", *Plant Mol.Biol.* 9: 3–17 (1987), Lerner et al., *Plant Physiol.*91: 124–129 (1989), Fontes et al.,*Plant Cell* 3: 483–496 (1991), Matsuoka et al., *Proc. Natl. Acad. Sci.* 88: 834 (1991), Gould et al., *J. Cell Biol* 108: 1657 (1989), Creissen et al., *Plant J.* 2: 129 (1991), Kalderon, D., Robers, B., Richardson, W., and Smith A., "A short amino acid sequence able to specify nuclear location", *Cell* 39: 499–509 (1984), Stiefel, V., Ruiz-Avila, L., Raz R., Valles M., Gomez J., Pages M., Martinez-Izquierdo J., Ludevid M., Landale J., Nelson T., and Puigdomenech P., "Expression of a maize cell wall hydroxyproline-rich glycoprotein gene in early leaf and root vascular differentiation", *Plant Cell* 2: 785–793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.* 114: 92–6 (1981).

According to a preferred embodiment, the transgenic plant provided for commercial production of foreign protein is a soybean plant. In another preferred embodiment, the biomass of interest is seed. For the relatively small number of transgenic plants that show higher levels of expression, a genetic map can be generated, primarily via conventional RFLP, PCR, and SSR analysis, which identifies the approximate chromosomal location of the integrated DNA molecule. For exemplary methodologies in this regard, see Glick and Thompson, METHODS IN PLANT MOLECULAR BIOLOGY AND BIOTECHNOLOGY 269–284 (CRC Press, Boca Raton, 1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below.

1. Genes that Confer Resistance to Pests or Disease and that Encode (A) Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. See, for example Jones et al., Science 266: 789 (1994) (cloning of the tomato Cf-9 gene for resistance to *Cladosporium fulvum*); Martin et al., Science 262: 1432 (1993) (tomato Pto gene for resistance to *Pseudomonas syringae* pv. tomato encodes a protein kinase); Mindrinos et al., Cell 78: 1089 (1994) (Arabidopsis RSP2 gene for resistance to *Pseudomonas syringae*).

(B) A gene conferring resistance to a pest, such as soybean cyst nematode. See e.g. PCT Application WO96/30517; PCT Application WO93/19181.

(C) A *Bacillus thuringiensis* protein, a derivative thereof or a synthetic polypeptide modeled thereon. See, for example, Geiser et al., Gene 48: 109 (1986), who disclose the cloning and nucleotide sequence of a Bt δ-endotoxin gene. Moreover, DNA molecules encoding δ-endotoxin genes can be purchased from American Type Culture Collection (Manassas, Va.), for example, under ATCC Accession Nos. 40098, 67136, 31995 and 31998.

(D) A lectin. See, for example, the disclosure by Van Damme et al., Plant Molec. Biol. 24: 25 (1994), who disclose the nucleotide sequences of several *Clivia miniata* mannose-binding lectin genes.

(E) A vitamin-binding protein such as avidin. See PCT application US93/06487, the contents of which are hereby incorporated by reference. The application teaches the use of avidin and avidin homologues as larvicides against insect pests.

(F) An enzyme inhibitor, for example, a protease or proteinase inhibitor or an amylase inhibitor. See, for example, Abe et al., J. Biol. Chem. 262: 16793 (1987) (nucleotide sequence of rice cysteine proteinase inhibitor), Huub et al., Plant Molec. Biol. 21: 985 (1993) (nucleotide sequence of cDNA encoding tobacco proteinase inhibitor I), Sumitani et al., Biosci. Biotech. Biochem. 57: 1243 (1993) (nucleotide sequence of *Streptomyces nitrosporeus* α-amylase inhibitor) and U.S. Pat. No. 5,494,813 (Hepher and Atkinson, issued Feb. 27, 1996).

(G) An insect-specific hormone or pheromone such as an ecdysteroid and juvenile hormone, a variant thereof, a mimetic based thereon, or an antagonist or agonist thereof. See, for example, the disclosure by Hammock et al., Nature 344: 458 (1990), of baculovirus expression of cloned juvenile hormone esterase, an inactivator of juvenile hormone.

(H) An insect-specific peptide or neuropeptide which, upon expression, disrupts the physiology of the affected pest. For example, see the disclosures of Regan, J. Biol. Chem. 269: 9 (1994) (expression cloning yields DNA coding for insect diuretic hormone receptor), and Pratt et al., Biochem. Biophys. Res. Comm. 163: 1243 (1989) (an allostatin is identified in *Diploptera puntata*). See also U.S. Pat. No. 5,266,317 to Tomalski et al., who disclose genes encoding insect-specific, paralytic neurotoxins.

(I) An insect-specific venom produced in nature by a snake, a wasp, etc. For example, see Pang et al., Gene 116: 165 (1992), for disclosure of heterologous expression in plants of a gene coding for a scorpion insectotoxic peptide.

(J) An enzyme responsible for an hyperaccumulation of a monterpene, a sesquiterpene, a steroid, hydroxamic acid, a phenylpropanoid derivative or another non-protein molecule with insecticidal activity.

(K) An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., Insect Biochem. Molec. Biol.23: 691 (1993), who teach the nucleotide sequence of a cDNA encoding tobacco hookworm chitinase, and Kawalleck et al., Plant Molec. Biol. 21: 673 (1993), who provide the nucleotide sequence of the parsley ubi4-2 polyubiquitin gene.

(L) A molecule that stimulates signal transduction. For example, see the disclosure by Botella et al., Plant Molec. Biol. 24: 757 (1994), of nucleotide sequences for mung bean calmodulin cDNA clones, and Griess et al., Plant Physiol.104: 1467 (1994), who provide the nucleotide sequence of a maize calmodulin cDNA clone.

(M) A hydrophobic moment peptide. See PCT application WO95/16776 (disclosure of peptide derivatives of Tachyplesin which inhibit fungal plant pathogens) and PCT application WO95/18855 (teaches synthetic antimicrobial peptides that confer disease resistance), the respective contents of which are hereby incorporated by reference.

(N) A membrane permease, a channel former or a channel blocker. For example, see the disclosure by Jaynes et al., Plant Sci. 89: 43 (1993), of heterologous expression of a cecropin-β lytic peptide analog to render transgenic tobacco plants resistant to *Pseudomonas solanacearum*.

(O) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., Ann. Rev. Phytopathol.28: 451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

(P) An insect-specific antibody or an immunotoxin derived therefrom. Thus, an antibody targeted to a critical metabolic function in the insect gut would inactivate an affected enzyme, killing the insect. Cf. Taylor et al., Abstract #497, SEVENTH INT'L SYMPOSIUM ON MOLECULAR PLANT-MICROBE INTERACTIONS (Edinburgh, Scotland, 1994) (enzymatic inactivation in transgenic tobacco via production of single-chain antibody fragments).

(Q) A virus-specific antibody. See, for example, Tavladoraki et al., Nature 366: 469 (1993), who show that transgenic plants expressing recombinant antibody genes are protected from virus attack.

(R) A developmental-arrestive protein produced in nature by a pathogen or a parasite. Thus, fungal endo α-1,4-D-polygalacturonases facilitate fungal colonization and plant nutrient release by solubilizing plant cell wall homo-α-1,4-D-galacturonase. See Lamb et al., Bio/Technology 10: 1436 (1992). The cloning and characterization of a gene which encodes a bean endopolygalacturonase-inhibiting protein is described by Toubart et al., Plant J. 2: 367 (1992).

(S) A developmental-arrestive protein produced in nature by a plant. For example, Logemann et al., Bio/Technology 10: 305 (1992), have shown that transgenic plants expressing the barley ribosome-inactivating gene have an increased resistance to fungal disease.

2. Genes that Confer Resistance to a Herbicide, for Example (A) A herbicide that inhibits the growing point or meristem, such as an imidazalinone or a sulfonylurea. Exemplary genes in this category code for mutant ALS and HAS enzyme as described, for example, by Lee et al.,*EMBO J.* 7: 1241 (1988), and Miki et al., *Theor. Appl.Genet.* 80: 449 (1990), respectively.

(B) Glyphosate (resistance imparted by mutant 5-enolpyruvl-3-phosphikimate synthase (EPSP) and aroA genes, respectively) and other phosphono compounds such as glufosinate (phosphinothricin acetyl transferase, PAT) and *Streptomyces hygroscopicus* phosphinothricin-acetyl transferase, bar, genes), and pyridinoxy or phenoxy propionic acids and cycloshexones (ACCase inhibitor-encoding genes). See, for example, U.S. Pat. No. 4,940,835 to Shah et al., which discloses the nucleotide sequence of a form of EPSP which can confer glyphosate resistance. A DNA molecule encoding a mutant aroA gene can be obtained under ATCC accession No. 39256, and the nucleotide sequence of the mutant gene is disclosed in U.S. Pat. No. 4,769,061 to Comai. European patent application No. 0 333 033 to Kumada et al. and U.S. Pat. No. 4,975,374 to Goodman et al. disclose nucleotide sequences of glutamine synthetase genes which confer resistance to herbicides such as L-phosphinothricin. The nucleotide sequence of a phosphinothricin-acetyl-transferase gene is provided in European application No. 0 242 246 to Leemans et al. De Greef et al., *Bio/Technology* 7: 61 (1989), describe the production of transgenic plants that express chimeric bar genes coding for phosphinothricin acetyl transferase activity. Exemplary of genes conferring resistance to phenoxy propionic acids and cycloshexones, such as sethoxydim and haloxyfop, are the Acc1-S1, Acc1-S2 and Acc1-S3 genes described by Marshall et al., *Theor. Appl. Genet.* 83: 435 (1992).

(C) A herbicide that inhibits photosynthesis, such as a triazine (psbA and gs$^+$ genes) and a benzonitrile (nitrilase gene). Przibilla et al., *Plant Cell* 3: 169 (1991), describe the transformation of Chlamydomonas with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441 and 67442. Cloning and expression of DNA coding for a glutathione S-transferase is described by Hayes et al., *Biochem. J.* 285: 173 (1992).

3. Genes that Confer or Contribute to a Value-added Trait, such as (A) Modified fatty acid metabolism, for example, by transforming a plant with an antisense gene of stearoyl-ACP desaturase to increase stearic acid content of the plant. See Knultzon et al., *Proc. Nat'l. Acad. Sci. USA* 89: 2624 (1992).

(B) Decreased phytate content (1) Introduction of a phytase-encoding gene would enhance breakdown of phytate, adding more free phosphate to the transformed plant. For example, see Van Hartingsveldt et al., *Gene* 127: 87 (1993), for a disclosure of the nucleotide sequence of an *Aspergillus niger* phytase gene.

(2) A gene could be introduced that reduces phytate content. In maize, this, for example, could be accomplished, by cloning and then reintroducing DNA associated with the single allele which is responsible for maize mutants characterized by low levels of phytic acid. See Raboy et al., *Maydica* 35: 383 (1990).

(C) Modified carbohydrate composition effected, for example, by transforming plants with a gene coding for an enzyme that alters the branching pattern of starch. See Shiroza et al., *J. Bacteriol.* 170: 810 (1988) (nucleotide sequence of *Streptococcus mutans* fructosyltransferase gene), Steinmetz et al., *Mol. Gen. Genet.* 200: 220 (1985) (nucleotide sequence of *Bacillus subtilis* levansucrase gene), Pen et al., *Bio/Technology* 10: 292 (1992) (production of transgenic plants that express *Bacillus licheniformis* α-amylase), Elliot et al., *Plant Molec. Biol.* 21: 515 (1993) (nucleotide sequences of tomato invertase genes), Søgaard et al., *J. Biol. Chem.* 268: 22480 (1993) (site-directed mutagenesis of barley α-amylase gene), and Fisher et al., *Plant Physiol.* 102: 1045 (1993) (maize endosperm starch branching enzyme II).

Methods for Soybean Transformation

Numerous methods for plant transformation have been developed, including biological and physical, plant transformation protocols. See, for example, Miki et al., "Procedures for Introducing Foreign DNA into Plants" in *Methods in Plant Molecular Biology and Biotechnology*, Glick, B. R. and Thompson, J. E. Eds. (CRC Press, Inc., Boca Raton, 1993) pages 67–88. In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick, B. R. and Thompson, J. E. Eds. (CRC Press, Inc., Boca Raton, 1993) pages 89–119.

A. Agrobacterium-mediated Transformation

One method for introducing an expression vector into plants is based on the natural transformation system of Agrobacterium. See, for example, Horsch et al., *Science* 227: 1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant. Sci.*10: 1 (1991). Descriptions of Agrobacterium vector systems and methods for Agrobacterium-mediated gene transfer are provided by Gruber et al., supra, Miki et al., supra, and Moloney et al., *Plant Cell Reports* 8: 238 (1989). See also, U.S. Pat. No. 5,563,055, (Townsend and Thomas), issued Oct. 8, 1996.

B. Direct Gene Transfer

Several methods of plant transformation, collectively referred to as direct gene transfer, have been developed as an alternative to Agrobacterium-mediated transformation. A generally applicable method of plant transformation is microprojectile-mediated transformation wherein DNA is carried on the surface of microprojectiles measuring 1 to 4 μm. The expression vector is introduced into plant tissues with a biolistic device that accelerates the microprojectiles to speeds of 300 to 600 m/s which is sufficient to penetrate plant cell walls and membranes. Sanford et al., *Part. Sci. Technol.* 5: 27 (1987), Sanford, J. C., *Trends Biotech.* 6: 299 (1988), Klein et al., *Bio/Technology* 6: 559–563 (1988), Sanford, J. C., *Physiol Plant* 79: 206 (1990), Klein et al., *Biotechnology* 10: 268 (1992). See also U.S. Pat. No. 5,015,580 (Christou, et a), issued May 14, 1991; U.S. Pat. No. 5,322,783 (Tomes, et al.), issued Jun. 21, 1994.

Another method for physical delivery of DNA to plants is sonication of target cells. Zhang et al., *Bio/Technology* 9: 996 (1991). Alternatively, liposome or spheroplast fusion have been used to introduce expression vectors into plants. Deshayes et al., *EMBO J.*, 4: 2731 (1985), Christou et al., *Proc Natl. Acad. Sci. U.S.A.* 84: 3962 (1987). Direct uptake of DNA into protoplasts using CaCl2 precipitation, polyvinyl alcohol or poly-L-ornithine have also been reported. Hain et al., *Mol. Gen. Genet.*199: 161 (1985) and Draper et al., *Plant Cell Physiol.*23: 451 (1982). Electroporation of protoplasts and whole cells and tissues have also been described. Donn et al., In Abstracts of VIIth International Congress on Plant Cell and Tissue Culture IAPTC, A2-38, p 53 (1990); D'Halluin et al., *Plant Cell* 4: 1495–1505 (1992) and Spencer et al., *Plant Mol. Biol.* 24: 51–61 (1994).

Following transformation of soybean target tissues, expression of the above-described selectable marker genes allows for preferential selection of transformed cells, tissues and/or plants, using regeneration and selection methods now well known in the art.

The foregoing methods for transformation would typically be used for producing a transgenic variety. The transgenic variety could then be crossed, with another (non-transformed or transformed) variety, in order to produce a new transgenic variety. Alternatively, a genetic trait which has been engineered into a particular soybean line using the foregoing transformation techniques could be moved into another line using traditional backcrossing techniques that are well known in the plant breeding arts. For example, a backcrossing approach could be used to move an engineered trait from a public, non-elite variety into an elite variety, or from a variety containing a foreign gene in its genome into a variety or varieties which do not contain that gene. As used herein, "crossing" can refer to a simple X by Y cross, or the process of backcrossing, depending on the context.

Tissue Culture of Soybeans

Further reproduction of the variety can occur by tissue culture and regeneration. Tissue culture of various tissues of soybeans and regeneration of plants therefrom is well known and widely published. For example, reference may be had to Komatsuda, T. et al., "Genotype X Sucrose Interactions for Somatic Embryogenesis in Soybean," *Crop Sci.* 31:333–337 (1991); Stephens, P. A. et al., "Agronomic Evaluation of Tissue-Culture-Derived Soybean Plants," *Theor. Appl. Genet. (*1991) 82:633–635; Komatsuda, T. et al., "Maturation and Germination of Somatic Embryos as Affected by Sucrose and Plant Growth Regulators in Soybeans *Glycine gracilis* Skvortz and *Glycine max* (L.) Merr.," *Plant Cell, Tissue and Organ Culture,* 28:103–113 (1992); Dhir, S. et al., "Regeneration of Fertile Plants from Protoplasts of Soybean (*Glycine max* L. Merr.): Genotypic Differences in Culture Response," *Plant Cell Reports* (1992) 11:285–289; Pandey, P. et al., "Plant Regeneration from Leaf and Hypocotyl Explants of *Glycine wightii* (W. and A.) VERDC. var. *longicauda,"Japan J. Breed.* 42:1–5 (1992); and Shetty, K., et al., "Stimulation of In Vitro Shoot Organogenesis in *Glycine max* (Merrill.) by Allantoin and Amides," Plant Science 81:(1992) 245–251; as well as U.S. Pat. No. 5,024,944, issued Jun. 18, 1991 to Collins et al. and U.S. Pat. No. 5,008,200, issued Apr. 16, 1991 to Ranch et al., the disclosures of which are hereby incorporated herein in their entirety by reference. Thus, another aspect of this invention is to provide cells which upon growth and differentiation produce soybean plants having the physiological and morphological characteristics of soybean variety 93B07.

This invention also is directed to methods for producing a soybean plant by crossing a first parent soybean plant with a second parent soybean plant wherein the first or second parent soybean plant is a soybean plant of the variety 93B07. Further, both first and second parent soybean plants can come from the soybean variety 93B07. Thus, any such methods using the soybean variety 93B07 are part of this invention: selfing, backcrosses, hybrid production, crosses to populations, and the like. All plants produced using soybean variety 93B07 as a parent are within the scope of this invention, including those developed from varieties derived from soybean variety 93B07. Advantageously, the soybean variety could be used in crosses with other, different, soybean plants to produce first generation ($F_1$) soybean hybrid seeds and plants with superior characteristics. The variety of the invention can also be used for transformation where exogenous genes are introduced and expressed by the variety of the invention. Genetic variants created either through traditional breeding methods using variety 93B07 or through transformation of 93B07 by any of a number of protocols known to those of skill in the art are intended to be within the scope of this invention.

As used herein, the term plant includes plant cells, plant protoplasts, plant cell tissue cultures from which soybean plants can be regenerated, plant calli, plant clumps, and plant cells that are intact in plants or parts of plants, such as embryos, pollen, ovules, seeds, flowers, pods, leaves, roots, root tips, anthers, and the like.

Industrial Applicability

The seed of soybean variety 93B07, the plant produced from the seed, the hybrid soybean plant produced from the crossing of the variety with any other soybean plant, hybrid seed, and various parts of the hybrid soybean plant can be utilized for human food, livestock feed, and as a raw material in industry.

The soybean is the world's leading source of vegetable oil and protein meal. The oil extracted from soybeans is used for cooking oil, margarine, and salad dressings. Soybean oil is composed of saturated, monounsaturated and polyunsaturated fatty acids. It has a typical composition of 11% palmitic, 4% stearic, 25% oleic, 50% linoleic and 9% linolenic fatty acid content ("Economic Implications of Modified Soybean Traits Summary Report", Iowa Soybean Promotion Board & American Soybean Association Special Report 92S, May 1990). Changes in fatty acid composition for improved oxidative stability and nutrition are constantly sought after. Industrial uses of soybean oil which is subjected to further processing include ingredients for paints, plastics, fibers, detergents, cosmetics, and lubricants. Soybean oil may be split, inter-esterified, sulfurized, epoxidized, polymerized, ethoxylated, or cleaved. Designing and producing soybean oil derivatives with improved functionality, oliochemistry, is a rapidly growing field. The typical mixture of triglycerides is usually split and separated into pure fatty acids, which are then combined with petroleum-derived alcohols or acids, nitrogen, sulfonates, chlorine, or with fatty alcohols derived from fats and oils.

Soybean is also used as a food source for both animals and humans. Soybean is widely used as a source of protein for animal feeds for poultry, swine and cattle. During processing of whole soybeans, the fibrous hull is removed and the oil is extracted. The remaining soybean meal is a combination of carbohydrates and approximately 50% protein.

For human consumption soybean meal is made into soybean flour which is processed to protein concentrates used for meat extenders or specialty pet foods. Production of edible protein ingredients from soybean offers a healthy, less expensive replacement for animal protein in meats as well as dairy-type products.

PERFORMANCE EXAMPLES OF 93B07

In the examples that follow, the traits and characteristics of soybean variety 93B07 are given. The data collected on soybean variety 93B07 is presented for the key characteristics and traits.

The results in Table 2A compare variety 93B07 to another similarly adapted Pioneer soybean variety, 9363. The results show that variety 93B07 is earlier to mature with a significantly lower absolute maturity value as well as a significantly lower predicted relative maturity score than variety 9363. Variety 93B07 also demonstrates significantly shorter plant stature with a significantly higher resistance to plant lodging than variety 9363.

The results in Table 2B compare variety 93B07 to another similarly adapted Pioneer soybean variety, 9323. The results show that variety 93B07 exhibits a significantly higher seed oil content compared to variety 9323. The table has few repetitions of data from few locations, however, it is expected that other significant differences will be observed with additional data. Finally, although not demonstrated in the table, variety 93B07 exhibits a substantial degree of glyphosate resistance while 9323 does not.

The results in Table 2C compare variety 93B07 to another similarly adapted Pioneer soybean variety, 93B71. The results show that variety 93B07 is earlier to mature with a significantly lower absolute maturity as well as a significantly lower predicted relative maturity score than variety 93B71. Variety 93B07 also displays significantly shorter plant stature than variety 93B71 with a significantly superior resistance to plant lodging.

The results in Table 2D compare variety 93B07 to another similarly adapted Pioneer soybean variety, 93B25. According to the results variety 93B07 is somewhat lower yielding than but is earlier to mature with a significantly lower absolute maturity and a significantly lower predicted relative maturity score than variety 93B25. Variety 93B07 also exhibits significantly superior resistance to plant lodging than variety 93B25, while the two are not significantly different with respect to plant height.

The results in Table 2E compare variety 93B07 to another similarly adapted Pioneer soybean variety, 92B91. The results indicate that variety 93B07 exhibits a significantly shorter plant stature with significantly higher resistance to plant lodging than variety 92B91. The table has few repetitions of data from few locations, however, it is expected that other significant differences will be observed with additional data. Although not shown in the table, variety 93B07 exhibits a substantial degree of glyphosate resistance while variety 92B91 does not.

The results in Table 2F compare variety 93B07 to another similarly adapted Pioneer soybean variety, 93B01. The results show that variety 93B07 displays significantly taller plant stature than variety 93B01 and is somewhat more susceptible to lodging. Variety 93B07 also demonstrates a larger seed size with a significantly lower number of seeds per pound and demonstrates a significantly lower seed oil content when compared to variety 93B01.

The results in Table 2G compare variety 93B07 to another similarly adapted Pioneer soybean variety, 9281. According to the results, variety 93B07 is later to mature with a significantly higher absolute maturity and a significantly higher predicted relative maturity score than variety 9281. Variety 93B07 further exhibits a significantly taller plant stature and a significantly lower seed oil content when compared to variety 9281. In addition, 93B07 also exhibits significantly superior resistance to Brown Stem Rot than variety 9281. Finally, although not demonstrated in the table, variety 93B07 exhibits a substantial degree of glyphosate resistance while variety 9281 does not.

The results in Table 2H compare variety 93B07 to another similarly adapted Pioneer soybean variety, 93B11. According to the results, variety 93B07 exhibits significantly superior resistance to plant lodging than 93B11. Variety 93B07 further exhibits a significantly higher number of seeds per pound than variety 93B11. Variety 93B07 also exhibits a higher susceptibility to Sudden Death Syndrome than variety 93B11. Although not shown in the table, variety 93B07 exhibits a substantial degree of glyphosate resistance while variety 93B11 does not.

The results in Table 2I compare variety 93B07 to another similarly adapted Pioneer soybean variety, 93B34. According to the results, variety 93B07 is earlier to mature with a significantly lower absolute maturity and a significantly lower predicted relative maturity score than variety 93B34. Variety 93B07 further exhibits a significantly taller plant stature with similar resistance to plant lodging as variety 93B34. Variety 93B07 further demonstrates a significantly lower seed oil content and a significantly lower number of seeds per pound when compared to variety 93B34.

The results in Table 2J compare variety 93B07 to another similarly adapted Pioneer soybean variety, 93B53. According to the results, variety 93B07 is earlier to mature with a significantly lower absolute maturity and a significantly lower predicted relative maturity score than variety 93B53. The table has few repetitions of data from few locations, however, it is expected that other significant differences will be observed with additional data.

The results in Table 2K compare variety 93B07 to another similarly adapted Pioneer soybean variety, 93B51. According to the results, variety 93B07 is earlier to mature with a significantly lower absolute maturity and a significantly lower predicted relative maturity score than variety 93B51. Variety 93B07 further exhibits a significantly superior resistance to plant lodging than variety 93B51. Finally variety 93B07 exhibits a significantly higher seed protein content than variety 93B51.

The results in Table 2L compare variety 93B07 to another similarly adapted Pioneer soybean variety, 9306. According to the results, variety 93B07 exhibits a significantly taller plant stature with similar resistance to lodging when compared to variety 9306. Variety 93B07 also demonstrates a significantly lower seed protein and a significantly lower seed oil content than variety 9306. In addition, 93B07 also exhibits larger seed size with a significantly lower number of seeds per pound than variety 9306. Finally, although not demonstrated in the table, variety 93B07 exhibits a substantial degree of glyphosate resistance while variety 9306 does not.

TABLE 2A

PAIRED COMPARISON REPORT
VARIETY #1 = 93B07
VARIETY #2 = 9363

|  | B/A | MAT ABS | PRM | HGT | LDG | PRO |
|---|---|---|---|---|---|---|
| 93B07 | 47.8 | 129.5 | 31 | 35.6 | 7.8 | 41.2 |
| 9363 | 47.9 | 134.5 | 35 | 39.3 | 6.1 | 42.4 |
| LOCS | 22 | 16 | 5 | 11 | 8 | 6 |
| DIFF | 0.1 | 5.0 | 5 | 3.7 | 1.6 | 1.2 |
| PROB | .944 | .000# | .000# | .001# | .006# | .063* |

|  | OIL | S/LB | BSR | PRT LAB | FECL ABS | SDS |
|---|---|---|---|---|---|---|
| 93B07 | 22.1 | 2841.0 | 7.3 | 5.3 | 5.3 | 6.0 |
| 9323 | 21.5 | 2899.7 | 5.4 | 5.7 | 4.6 | 3.0 |
| LOCS | 6 | 5 | 4 | 2 | 2 | 1 |
| DIFF | 0.6 | 58.7 | 1.9 | 0.3 | 0.6 | 3.0 |
| PROB | .053* | .481 | .108 | .705 | .500 |  |

*significant at the 10% level
+significant at the 5% level
significant at the 1% level

TABLE 2B

PAIRED COMPARISON REPORT
VARIETY #1 = 93B07
VARIETY #2 = 9323

| | B/A | MAT ABS | PRM | HGT | LDG | PRO |
|---|---|---|---|---|---|---|
| 93B07 | 48.2 | 127.9 | 30 | 37 | 7.3 | 40.2 |
| 9323 | 48.5 | 129.7 | 32 | 36.2 | 7.7 | 42.1 |
| LOCS | 24 | 11 | 6 | 9 | 6 | 2 |
| DIFF | 0.3 | 1.8 | 2 | 0.8 | 0.3 | 1.9 |
| PROB | 0.859 | 0.109 | 0.262 | 0.376 | 0.363 | .067* |

| | OIL | S/LB | BSR | PRT LAB | WHD FLD | SDS | SLF |
|---|---|---|---|---|---|---|---|
| 93B07 | 22.4 | 2856.2 | 7.7 | 3.7 | 7 | 5.7 | 8 |
| 9323 | 21.4 | 3003.5 | 8.3 | 4 | 6.5 | 4 | 8 |
| LOCS | 2 | 2 | 3 | 1 | 1 | 1 | 1 |
| DIFF | 1 | 147.2 | 0.7 | 0.3 | 0.5 | 1.7 | 0 |
| PROB | .000# | .084* | 0.184 | | | | |

*significant at the 10% level
+significant at the 5% level
significant at the 1% level

TABLE 2C

PAIRED COMPARISON REPORT
VARIETY #1 = 93B07
VARIETY #2 = 93B71

| | B/A | MAT ABS | PRM | HGT | LDG | PRO |
|---|---|---|---|---|---|---|
| 93B07 | 48.3 | 123.2 | 30 | 37.2 | 7.4 | 40.1 |
| 93B71 | 49.7 | 129.4 | 37 | 42.1 | 6.3 | 40.6 |
| LOCS | 22 | 9 | 6 | 9 | 6 | 1 |
| DIFF | 1.4 | 6.2 | 7 | 4.8 | 1.2 | 0.5 |
| PROB | .0.33 | .000# | .000# | .005# | .013+ | |

| | OIL | S/LB | BSR | PRT LAB | WHD FLD | SDS | SLF |
|---|---|---|---|---|---|---|---|
| 93B07 | 23 | 2856.2 | 7 | 3.7 | 7 | 5.7 | 8 |
| 93B71 | 21.3 | 2898.2 | 7 | 2.7 | 7 | 2.3 | 9 |
| LOCS | 1 | 2 | 1 | 1 | 1 | 1 | 1 |
| DIFF | 1.7 | 42 | 0 | 1 | 0 | 3.3 | 1 |
| PROB | | 0.5 | | | | | |

*significant at the 10% level
+significant at the 5% level
significant at the 1% level

TABLE 2D

PAIRED COMPARISON REPORT
VARIETY #1 = 93B07
VARIETY #2 = 93B25

| | B/A | MAT ABS | PRM | HGT | LDG | PRO |
|---|---|---|---|---|---|---|
| 93B07 | 47.5 | 127.2 | 30 | 37.1 | 7.4 | 41 |
| 93B25 | 50 | 128.5 | 31 | 36.4 | 6.8 | 40.6 |
| LOCS | 44 | 23 | 11 | 17 | 12 | 7 |
| DIFF | 2.4 | 1.3 | 1 | 0.7 | 0.6 | 0.4 |
| PROB | .020+ | .006# | .020+ | 0.152 | .041+ | 0.574 |

| | OIL | S/LB | BSR | PRT LAB | WHD FLD | SDS | SLF |
|---|---|---|---|---|---|---|---|
| 93B07 | 22.2 | 2845.4 | 7.2 | 4.1 | 7 | 5.2 | 8 |
| 93B25 | 22.1 | 2903.4 | 8.5 | 2.8 | 7 | 6.6 | 8 |

TABLE 2D-continued

PAIRED COMPARISON REPORT
VARIETY #1 = 93B07
VARIETY #2 = 93B25

| | | | | | | | |
|---|---|---|---|---|---|---|---|
| LOCS | 7 | 7 | 5 | 2 | 1 | 3 | 1 |
| DIFF | 0.1 | 58 | 1.3 | 1.2 | 0 | 1.3 | 0 |
| PROB | 0.798 | 0.487 | 0.193 | 0.5 | | 0.423 | |

*significant at the 10% level
+significant at the 5% level
significant at the 1% level

TABLE 2E

PAIRED COMPARISON REPORT
VARIETY #1 = 93B07
VARIETY #2 = 92B91

| | B/A | MAT ABS | PRM | HGT | LDG | PRO |
|---|---|---|---|---|---|---|
| 93B07 | 48.5 | 121.6 | 30 | 36.6 | 7.4 | 40.1 |
| 92B91 | 50.4 | 121.5 | 30 | 40.4 | 4 | 41.3 |
| LOCS | 25 | 10 | 6 | 9 | 5 | 1 |
| DIFF | 2 | 0.1 | 0 | 3.9 | 3.4 | 1.2 |
| PROB | 0.176 | 0.913 | 0.763 | .003# | .007# | |

| | OIL | S/LB | BSR | PRTLAB | WHD FLD | SDS |
|---|---|---|---|---|---|---|
| 93B07 | 23 | 2856.2 | 7 | 3.7 | 7 | 4.8 |
| 92B91 | 23.5 | 3086.9 | 9 | 4.3 | 7 | 8.8 |
| LOCS | 1 | 2 | 1 | 1 | 1 | 2 |
| DIFF | 0.5 | 230.7 | 2 | 0.7 | 0 | 3.9 |
| PROB | | 0.316 | | | | .094* |

*significant at the 10% level
+significant at the 5% level
significant at the 1% level

TABLE 2F

PAIRED COMPARISON REPORT
VARIETY #1 = 93B07
VARIETY #2 = 93B01

| | B/A | MAT ABS | PRM | HGT | LDG | PRO |
|---|---|---|---|---|---|---|
| 93B07 | 47.5 | 127.2 | 30 | 37.1 | 7.4 | 41 |
| 93B01 | 50.5 | 127.2 | 30 | 31.6 | 8.3 | 40.6 |
| LOCS | 44 | 23 | 11 | 17 | 12 | 7 |
| DIFF | 3 | 0 | 0 | 5.5 | 1 | 0.4 |
| PROB | .001# | 0.913 | 0.962 | .000# | .006# | 0.132 |

| | OIL | S/LB | BSR | PRT LAB | WHD FLD | SDS |
|---|---|---|---|---|---|---|
| 93B07 | 22.2 | 2845.4 | 7.2 | 4.1 | 7 | 5.2 |
| 93B01 | 23.8 | 3300.8 | 5.6 | 3.6 | 5 | 5.2 |
| LOCS | 7 | 7 | 5 | 2 | 1 | 3 |
| DIFF | 1.6 | 455.4 | 1.6 | 0.5 | 2 | 0.1 |
| PROB | .000# | .000# | .078* | 0.5 | | 0.971 |

*significant at the 10% level
+significant at the 5% level
significant at the 1% level

TABLE 2G

PAIRED COMPARISON REPORT
VARIETY #1 = 93B07
VARIETY #2 = 9281

|       | B/A  | MAT ABS | PRM   | HGT   | LDG  | PRO   |
|-------|------|---------|-------|-------|------|-------|
| 93B07 | 47.3 | 127.6   | 30    | 37    | 7.4  | 41    |
| 9281  | 51.5 | 125.7   | 29    | 31.4  | 7.8  | 41.3  |
| LOCS  | 42   | 22      | 10    | 16    | 11   | 7     |
| DIFF  | 4.3  | 2       | 2     | 5.7   | 0.5  | 0.3   |
| PROB  | .000# | .000#  | .035+ | .000# | 0.148 | 0.443 |

|       | OIL  | S/LB   | BSR   | PRT LAB | WHD FLD | SDS   |
|-------|------|--------|-------|---------|---------|-------|
| 93B07 | 22.2 | 2845.4 | 7.2   | 4.1     | 7       | 5.2   |
| 9281  | 23.8 | 2887.6 | 5.4   | 3.6     | 7.5     | 4.6   |
| LOCS  | 7    | 7      | 5     | 2       | 1       | 3     |
| DIFF  | 1.6  | 42.3   | 1.8   | 0.5     | 0.5     | 0.7   |
| PROB  | .000# | 0.385 | .037+ | 0.5     |         | 0.184 |

*significant at the 10% level
+significant at the 5% level
significant at the 1% level

TABLE 2H

PAIRED COMPARISON REPORT
VARIETY #1 = 93B07
VARIETY #2 = 93B11

|       | B/A  | MAT ABS | PRM   | HGT   | LDG   | PRO   |
|-------|------|---------|-------|-------|-------|-------|
| 93B07 | 47.3 | 127.6   | 30    | 37    | 7.4   | 41    |
| 93B11 | 50   | 127.4   | 30    | 35.7  | 6.4   | 39.9  |
| LOCS  | 42   | 22      | 10    | 16    | 1i    | 7     |
| DIFF  | 2.8  | 0.3     | 0     | 1.3   | 1     | 1.1   |
| PROB  | .000# | 0.49   | 0.751 | 0.111 | .020+ | 0.145 |

|       | OIL  | S/LB   | BSR   | PRT LAB | WHD FLD | SDS  | SLF   |
|-------|------|--------|-------|---------|---------|------|-------|
| 93B07 | 22.2 | 2845.4 | 7.2   | 4.1     | 7       | 5.2  | 8     |
| 93B11 | 22.8 | 2696.4 | 7.5   | 6A      | 7       | 8.3  | 8     |
| LOCS  | 7    | 7      | 5     | 2       | 1       | 3    | 1     |
| DIFF  | 0.6  | 149    | 0.3   | 2.3     | 0       | 3.1  | 0     |
| PROB  | 0.122 | .025+ | 0.374 | .090*   |         | .034+ |      |

*significant at the 10% level
+significant at the 5% level
significant at the 1% level

TABLE 2I

PAIRED COMPARISON REPORT
VARIETY #1 = 93B07
VARIETY #2 = 93B34

|       | B/A  | MAT ABS | PRM   | HGT   | LDG   | PRO   |
|-------|------|---------|-------|-------|-------|-------|
| 93B07 | 47.5 | 127.2   | 30    | 37.1  | 7.4   | 41    |
| 93B34 | 51.3 | 130.1   | 33    | 33.5  | 7.6   | 39.9  |
| LOCS  | 44   | 23      | 11    | 17    | 12    | 7     |
| DIFF  | 3.8  | 2.9     | 3     | 3.6   | 0.3   | 1.1   |
| PROB  | .000# | .000#  | .000# | .000# | 0.559 | 0.246 |

|       | OIL  | S/LB   | BSR   | PRT LAB | WHD FLD | SDS  | SLF |
|-------|------|--------|-------|---------|---------|------|-----|
| 93B07 | 22.2 | 2845.4 | 7.2   | 4.1     | 7       | 5.2  | 8   |
| 93B34 | 23.5 | 2938.5 | 5.6   | 2.8     | 6       | 5.3  | 8   |

TABLE 2I-continued

PAIRED COMPARISON REPORT
VARIETY #1 = 93B07
VARIETY #2 = 93B34

|       |       |        |       |      |      |       |      |
|-------|-------|--------|-------|------|------|-------|------|
| LOCS  | 7     | 7      | 5     | 2    | 1    | 3     | 1    |
| DIFF  | 1.2   | 93.2   | 1.6   | 1.2  | 1    | 0.1   | 0    |
| PROB  | .036+ | .018+  | .078* | 0.5  |      | 0.926 |      |

*significant at the 10% level
+significant at the 5% level
significant at the 1% level

TABLE 2J

PAIRED COMPARISON REPORT
VARIETY #1 = 93B07
VARIETY #2 = 93B53

|       | B/A  | MAT ABS | PRM   | HGT   | LDG   | PRO   |
|-------|------|---------|-------|-------|-------|-------|
| 93B07 | 48.8 | 121.3   | 30    | 36.7  | 7.4   | 40.1  |
| 93B53 | 52.9 | 126.3   | 35    | 36.2  | 6.8   | 40.3  |
| LOCS  | 27   | 11      | 7     | 10    | 6     | 1     |
| DIFF  | 4.1  | 5       | 5     | 0.5   | 0.6   | 0.2   |
| PROB  | .003# | .000#  | .000# | 0.563 | 0.22  |       |

|       | OIL  | S/LB   | BSR   | PRT LAB | WHD FLD | SDS   | SLF |
|-------|------|--------|-------|---------|---------|-------|-----|
| 93B07 | 23   | 2856.2 | 7     | 3.7     | 7       | 4.8   | 8   |
| 93B53 | 23.8 | 2761.9 | 5     | 3.7     | 5.5     | 4.9   | 8   |
| LOCS  | 1    | 2      | 1     | 1       | 1       | 2     | 1   |
| DIFF  | 0.8  | 94.3   | 2     | 0       | 1.5     | 0.1   | 0   |
| PROB  |      | 0.331  |       |         |         | 0.963 |     |

*significant at the 10% level
+significant at the 5% level
significant at the 1% level

TABLE 2K

PAIRED COMPARISON REPORT
VARIETY #1 = 93B07
VARIETY #2 = 93B51

|       | B/A  | MAT ABS | PRM   | HGT   | LDG   | PRO   |
|-------|------|---------|-------|-------|-------|-------|
| 93B07 | 47.5 | 127.2   | 30    | 37.1  | 7.4   | 41    |
| 93B51 | 53   | 132     | 35    | 37.7  | 6.3   | 39.2  |
| LOCS  | 44   | 23      | 11    | 17    | 12    | 7     |
| DIFF  | 5.5  | 4.8     | 5     | 0.6   | 1     | 1.8   |
| PROB  | .000# | .000#  | .000# | 0.22  | .009# | .017+ |

|       | OIL  | S/LB   | BSR   | PRT LAB | WHD FLD | SDS   | SLF |
|-------|------|--------|-------|---------|---------|-------|-----|
| 93B07 | 22.2 | 2845.4 | 7.2   | 4.1     | 7       | 5.2   | 8   |
| 93B51 | 22.6 | 2849.1 | 7.8   | 3.4     | 7       | 4.5   | 7   |
| LOCS  | 7    | 7      | 5     | 2       | 1       | 3     | 1   |
| DIFF  | 0.4  | 3.7    | 0.6   | 0.7     | 0       | 0.7   | 1   |
| PROB  | 0.38 | 0.885  | 0.529 | 0.295   |         | 0.634 |     |

*significant at the 10% level
+significant at the 5% level
significant at the 1% level

TABLE 2L

PAIRED COMPARISON REPORT
VARIETY #1 = 93B07
VARIETY #2 = 9306

|       | B/A  | MAT ABS | PRM  | HGT  | LDG  | PRO  |
|-------|------|---------|------|------|------|------|
| 93B07 | 47.3 | 127.6   | 30   | 37   | 7.4  | 41   |
| 9306  | 52.2 | 119.7   | 31   | 33.6 | 6.3  | 42   |
| LOCS  | 42   | 22      | 10   | 16   | 11   | 7    |
| DIFF  | 4.9  | 7.9     | 1    | 3.4  | 1.1  | 1    |
| PROB  | .000# | 0.361  | 0.24 | .000# | 0.126 | .012+ |

|       | OIL   | S/LB   | BSR  | PRT LAB | WHD FLD | SDS  | SLF   |
|-------|-------|--------|------|---------|---------|------|-------|
| 93B07 | 22.2  | 2845.4 | 7.2  | 4.1     | 7       |      | 5.2   |
| 9306  | 24.2  | 2997.7 | 8.6  | 2.9     | 4.5     |      | 8.4   |
| LOCS  | 7     | 7      | 5    | 2       | 1       |      | 3     |
| DIFF  | 2     | 152.3  | 1.6  | 1.2     | 2.5     |      | 3.2   |
| PROB  | .001# | .018+  | 0.14 | .090*   |         |      | .071* |

*significant at the 10% level
+significant at the 5% level
significant at the 1% level Deposits Applicant has made a deposit of at least 2500 seeds of Soybean Variety 93B07 with the American Type Culture Collection (ATCC), Manassas, Va. 20110 USA, ATCC Deposit No. PTA-2107. The seeds deposited with the ATCC on Jun. 20, 2000 were taken from the deposit maintained by Pioneer Hi-Bred International, Inc., 800 Capital Square, 400 Locust Street, Des Moines, Iowa 50309-2340 since prior to the filing date of this application. This deposit of the Soybean Variety 93B07 will be maintained in the ATCC depository, which is a public depository, for a period of 30 years, or 5 years after the most recent request, or for the effective life of the patent, whichever is longer, and will be replaced if it becomes nonviable during that period. Additionally, Applicant has satisfied all the requirements of 37 C.F.R. §§1.801–1.809, including providing an indication of the viability of the sample. Applicant imposes no restrictions on the availability of the deposited material from the ATCC; however, Applicant has no authority to waive any restrictions imposed by law on the transfer of biological material or its transportation in commerce. Applicant does not waive any infringement of his rights granted under this patent or under the Plant Variety Protection Act (7 USC 2321 et seq.). U.S. Plant Variety Protection of Soybean Variety 93B07 has been applied for under Application No. 200000046.

The foregoing invention has been described in detail by way of illustration and example for purposes of clarity and understanding. However, it will be obvious that certain changes and modifications such as single gene modifications and mutations, somoclonal variants, variant individuals selected from large populations of the plants of the instant variety and the like may be practiced within the scope of the invention, as limited only by the scope of the appended claims.

What is claimed is:

1. A soybean seed designated 93B07, representative seed of said soybean variety 93B07 having been deposited under ATCC Accession No. PTA-2107.

2. A soybean plant, or parts thereof, produced by growing the seed of claim 1.

3. Pollen of the plant of claim 2.

4. An ovule of the plant of claim 2.

5. A soybean plant, or parts thereof, having all the physiological and morphological characteristics of the plant of claim 2.

6. A tissue culture of regenerable cells from the plant of claim 2.

7. A tissue culture according to claim 6, the cells or protoplasts of the tissue culture being of a tissue selected from the group consisting of: leaf, pollen, cotyledon, hypocotyl, embryos, root, pod, flower, shoot and stalk.

8. A soybean plant regenerated from the tissue culture of claim 6, capable of expressing all the morphological and physiological characteristics of soybean variety 93B07, representative seed of said soybean variety 93B07 having been deposited under ATCC Accession No. PTA-2107.

9. A soybean plant with all of the physiological and morphological characteristics of the soybean plant of claim 2, said soybean plant produced by the tissue culture process using soybean plant of claim 2 as the starting material for such a process.

10. A method for producing a first generation hybrid soybean seed comprising crossing the plant of claim 2 with a different inbred parent soybean plant and harvesting the resultant first generation hybrid soybean seed.

11. A method for producing a first generation hybrid soybean seed comprising crossing the plant of claim 2 with a different inbred parent soybean plant and harvesting the resultant first generation hybrid soybean seed, wherein the inbred soybean plant of claim 2 is the female parent.

12. A method for producing a first generation hybrid soybean seed comprising crossing the plant of claim 2 with a different inbred parent soybean plant and harvesting the resultant first generation hybrid soybean seed, wherein the inbred soybean plant of claim 2 is the male parent.

13. A method for producing a soybean variety 93B07-derived soybean plant, comprising:
    (a) crossing soybean variety 93B07, representative seed of said soybean variety 93B07 having been deposited under ATCC Accession No. PTA-2107 with a second soybean plant to yield progeny soybean seed; and
    (b) growing said progeny soybean seed, under plant growth conditions, to yield said soybean variety 93B07-derived soybean plant.

14. A soybean variety 93B07-derived soybean plant, or parts thereof, produced by the method of claim 13.

15. The method of claim 13, further comprising:
    (a) crossing said soybean variety 93B07-derived soybean plant with itself or another soybean plant to yield additional soybean variety 93B07-derived progeny soybean seed;
    (b) growing said progeny soybean seed of step (a) under plant growth conditions, to yield additional soybean variety 93B07-derived soybean plants; and
    (c) repeating the crossing and growing steps of (a) and (b) from 0 to 7 times to generate further soybean variety 93B07-derived soybean plants.

16. A soybean variety 93B07-derived soybean plant, or parts thereof, produced by the method of claim 15.

17. The soybean plant, or parts thereof, of claim 5, wherein the plant or parts thereof have been transformed so that its genetic material contains one or more transgenes operably linked to one or more regulatory elements.

18. A method for producing a soybean plant that contains in its genetic material one or more transgenes, comprising crossing the soybean plant of claim 17 with either a second plant of another soybean line, or a non-transformed soybean plant of the soybean variety 93B07, so that the genetic material of the progeny that result from the cross contains the transgene(s) operably linked to a regulatory element.

19. Soybean plants or parts thereof, produced by the method of claim 18.

20. An $F_1$ hybrid soybean seed produced by the method of claim 10.

21. An $F_1$ hybrid soybean plant or parts thereof produced by the seed of claim 20.

22. A method for developing a soybean plant in a soybean breeding program using plant breeding techniques, comprising:

using the soybean plant, or its parts, of claim 2 as a source of breeding material.

23. The method of claim 22 wherein said plant breeding techniques are selected from the group consisting of: recurrent selection, mass selection, bulk selection, backcrossing, pedigree breeding, restriction fragment length polymorphism enhanced selection, genetic marker enhanced selection, and transformation.

24. A method for developing a soybean plant in a soybean breeding program using plant breeding techniques, comprising: using the soybean plant, or its parts, of claim 5 as a source of breeding material.

25. The method of claim 24 wherein said plant breeding techniques are selected from the group consisting of: recurrent selection, mass selection, bulk selection, backcrossing, pedigree breeding, restriction fragment length polymorphism enhanced selection, genetic marker enhanced selection, and transformation.

26. A method for developing a soybean plant in a soybean breeding program using plant breeding techniques, comprising: using the soybean plant, or its parts, of claim 17 as a source of breeding material.

27. The method of claim 26 wherein said plant breeding techniques are selected from the group consisting of: recurrent selection, mass selection, bulk selection, backcrossing, pedigree breeding, restriction fragment length polymorphism enhanced selection, genetic marker enhanced selection, and transformation.

* * * * *